United States Patent [19]

Mulinos

[11] 4,291,030

[45] Sep. 22, 1981

[54] METHOD OF LOWERING BLOOD CHOLESTEROL

[75] Inventor: Michael G. Mulinos, Westfield, N.J.

[73] Assignee: Unimed, Inc., Somerville, N.J.

[21] Appl. No.: 172,132

[22] Filed: Jul. 25, 1980

[51] Int. Cl.³ .............................................. A61K 31/555
[52] U.S. Cl. ...................................................... 424/245
[58] Field of Search ........................................... 424/245

[56] References Cited

U.S. PATENT DOCUMENTS 3,825,546  7/1974  Rice ..................................... 546/4

OTHER PUBLICATIONS

Chem. Abstr.: 82: 112146b (1975).

Primary Examiner—Frank Cacciapaglia, Jr.
Attorney, Agent, or Firm—Steinberg and Raskin

[57] ABSTRACT

The cholesterol blood level is lowered by administration of a spirogermanium (dimethyl, diethyl, dipropyl or dibutyl, diethyl or dibutyl being preferred).

4 Claims, No Drawings

METHOD OF LOWERING BLOOD CHOLESTEROL

BACKGROUND OF THE INVENTION

Cholesterol is the principal animal sterol. It occurs in all tissues of the animal body. It is synthesized by all tissues in the body but is also taken in as part of fatty foods. Its concentration in the blood is from 150 to 250 mg per 100 ml and depends upon intake in the food and increases with age. Its main function in the blood is the transport of fats and fatty acids to and from the liver.

It is a common belief that there is a correlation between high levels of cholesterol in the blood and atherosclerosis, a disease of large arteries, characterized by plaque-like intimal deposits which contain neutral fat, cholesterol, and sometimes blood. This condition leads to gradual narrowing of the arterial lumen, ulceration of the intima. The development of a thrombus around the plaques can cause coronary disease, cerebral thrombosis (stroke), and peripheral arterial narrowing with gangrene.

Arteriosclerosis is the end result of atheromatosis; i.e., hardening of the arteries. Restriction of cholesterol intake in the food has been recommended to lower the blood cholesterol levels. This has not been generally effective because the synthesis of cholesterol in the body appears to supply the body's needs for cholesterol and can be only in part controlled by intake. On the other hand, the need for cholesterol is enhanced by increasing the fat in the diet, such as butter and animal fat, which then require higher amounts of cholesterol for their metabolism and transport in the body.

Several drugs have been introduced in attempts to control the amount of cholesterol in the blood, known as hypocholesterolemic agents. Such drugs have clinical utility for patients who do not respond to dietary treatment. The hypocholesterolemic effect of such drugs may result from interference with synthesis of cholesterol; from inhibition of its absorption from the digestive tract; from a hastening of its metabolic degradation or some as yet unknown type of action.

SUMMARY OF THE INVENTION

Generally speaking, in accordance with the present invention, it has been discovered that certain specific compounds disclosed in U.S. Pat. No. 3,825,546, namely a series of azaspiranes containing silicon or germanium in a ring, namely those azaspirances containing germanium in a ring, which are know as spirogermaniums, particularly the dimethyl, diethyl, dipropyl, and dibutyl spirogermaniums, including their acid addition salts and bis-quaternary salts, can be used for the lowering of blood cholesterol in animals.

It is accordingly a primary object of the present invention to provide for compositions and methods for the lowering of blood cholesterol in animals.

It is a further object of the present invention to provide for the lowering of blood level cholesterol in animals by the administration thereto of a blood level lowering effective amount of spirogermanium.

Other objects and advantages of the present invention will be apparent from a further reading of the specification and of the appended claims.

The compounds of U.S. Pat. No. 3,825,546 which can be used for the purposes of the present invention are those compounds of the following structural formula:

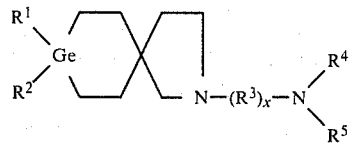

Wherein
$R^1$, $R^2$, $R^4$ and $R^5$ are the same or different alkyl groups of 1–4 carbon atoms
Ge = germanium
$R^3$ = alkylene or alkenylene
$X$ = 2–6 when $R^3$ is alkylene and 3–4 when $R^3$ is alkenylene as well as acid addition salts and bis-quaternary salts thereof.

The acid addition salts are of course the physiologically compatible acid addition salts, most preferably the dihydrochloride.

The bis-quaternary salts are of course the physiologically compatible bis-quaternary salts including the methiodide and the dimethiodide.

The dimethyl spirogermanium, diethyl spirogermanium, dipropyl spirogermanium and dibutyl spirogermanium which are topically effective in the lowering of cholesterol levels in the blood are:

N-(3-dimethylaminopropyl)-2-aza-8,8-dimethyl-8-germaspiro[4:5] decane;

N-(3-dimethylaminopropyl)-2-aza-8,8-diethyl-8-germaspiro[4:5] decane;

N-(3-dimethylaminopropyl)-2-aza-8,8-dipropyl-8-germaspiro[4:5] decane; and

N-(3-dimethylaminopropyl)-2-aza-8,8-dibutyl-8-germaspiro[4:5] decane.

As indicated previously, the above compounds may be utilized in the form of their acid addition salts or bisquaternary salts. Most preferred are the dihydrochloride salts.

The above compounds may be distributed in any suitable pharmaceutical carrier for administration by injection or for oral administration. Sterile aqueous solutions can be prepared of the non toxic salts which are soluble in water for administration by injection, for example intravenous administration or intraperitoneal injection, or for oral administration. It is preferred, however, for oral administration to utilize compositions in tablet or capsule form, for example tablets with lactose or the like as a carrier.

Although the spirogermaniums can be tolerated in rather high doses without any adverse effects, it having been found safe when given intravenously in doses of 50–100 mg/m² of body surface, and even doses of 120 mg/m² of body surface, much smaller doses can be administered for the purposes of the present invention to achieve the cholesterol blood level lowering effect. Doses of 25–50 mg/m² of body surface per day are suitable. The administration of the spirogermanium, either intravenously or orally is effective in lowering blood cholesterol and it is therefore possible to use the spirogermanium for the purpose of mitigating the atheromatous sequelae which accompany high blood cholesterol values.

It has been found that the spirogermaniums have the effect of lowering the blood cholesterol in laboratory animals without any apparent tissue damage, as shown by microscopic examination. The lowering of the blood cholesterol concentration ocurs during the course of intravenous injection in the dog and from intraperitoneal and oral administration in rats.

DESCRIPTION OF PREFERRED EMBODIMENTS

The following examples are given to further illustrate the present invention. The scope of the invention is not, however, meant to be limited to the specific details of the examples.

EXAMPLE 1

A composition for injection was prepared of diethyl spirogermanium dihydrochloride ($R^1$ and $R^2$=ethyl) dissolved in saline. The solution contained 100 mg of spirogermanium per each 10 ml saline.

The blood cholesterol levels of dogs were determined over a course of six months. The dogs were then given intravenous injections of the solution in doses corresponding to 100 mg/$m^2$ of body surface. Blood was then drawn periodically from the dogs and analyzed for blood cholesterol concentration. It was found that the administration of the spirogermanium results in a sustained and substantial lowering of the blood cholesterol values.

Results were duplicated by substituting dibutyl spirogermanium or dipropyl spirogermanium for the diethyl spirogermanium.

EXAMPLE 2

Oral compositions are prepared by forming tablets of diethyl spirogermanium and beta lactose or other suitable excipients with concentrations of 25 mg diethyl spirogermanium per tablet.

Oral administration of the spirogermanium to rats results in lowering of the blood cholesterol values of the rats.

EXAMPLE 3

The composition of Example 1 is administered by intraperitoneal injection to rats and is found to result in the lowering of blood cholesterol values.

It is apparent that variations and modifications of the invention as described above can be made.

What is claimed is:

1. Method of reducing blood cholesterol in an animal in need of such treatment, which comprises administering to said animal a blood cholesterol lowering effective amount of a spirogermanium selected from the group consisting of dimethyl spirogermanium, deithyl spirogermanium dipropyl spirogermanium and dibutyl spirogermanium.

2. Method according to claim 1 wherein the administration is by intravenous injection.

3. Method according to claim 1 wherein the administration is by intraperitoneal injection.

4. Method according to claim 1 wherein the administration is oral.

* * * * *